US009888937B2

(12) United States Patent
Gill et al.

(10) Patent No.: US 9,888,937 B2
(45) Date of Patent: *Feb. 13, 2018

(54) SYSTEM AND METHOD FOR MINIMALLY INVASIVE TISSUE TREATMENT USING ULTRASONIC CANNULA

(71) Applicant: Tenex Health, Inc., Lake Forest, CA (US)

(72) Inventors: Jagjit Gill, Lake Forest, CA (US); Darryl E. Barnes, Rochester, MN (US); Jay Smith, Rochester, MN (US); William Wilemon, Laguna Niguel, CA (US)

(73) Assignee: Tenex Health, Inc., Lake Forest, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/830,315

(22) Filed: Aug. 19, 2015

(65) Prior Publication Data

US 2015/0351790 A1    Dec. 10, 2015

Related U.S. Application Data

(63) Continuation of application No. 14/514,262, filed on Oct. 14, 2014, now Pat. No. 9,730,721, which is a
(Continued)

(51) Int. Cl.
*A61B 8/00* (2006.01)
*A61B 17/32* (2006.01)
(Continued)

(52) U.S. Cl.
CPC .... *A61B 17/320068* (2013.01); *A61B 8/4444* (2013.01); *A61B 17/3205* (2013.01);
(Continued)

(58) Field of Classification Search
CPC .... A61B 17/320068; A61B 2019/5276; A61B 2017/320084
See application file for complete search history.

(56) References Cited

U.S. PATENT DOCUMENTS

| 3,575,622 A | 4/1971 | Nielson et al. |
| 3,589,363 A | 6/1971 | Banko et al. |
(Continued)

FOREIGN PATENT DOCUMENTS

| CN | 2402273 Y | 10/2000 |
| CN | 2774407 Y | 4/2006 |
(Continued)

OTHER PUBLICATIONS

International Application No. PCT/US2016/032055 filed on May 12, 2016.
(Continued)

*Primary Examiner* — Serkan Akar
(74) *Attorney, Agent, or Firm* — K&L Gates LLP; Louis C. Cullman; Robert W. Winn (57) ABSTRACT

Delivering ultrasonic energy to a target musculoskeletal tissue site includes connecting a delivery device to a vacuum source, a fluid source, and a power signal source. The delivery device has a housing portion maintaining an ultrasound transducer and a tip portion having a sleeve and a cannula. The cannula is coupled to the ultrasound transducer and received in the sleeve to define a covered portion and an exposed portion. Ultrasonic energy is generated by sending a power signal from the power signal source to the ultrasound transducer. The ultrasonic energy is transmitted from the ultrasound transducer to the cannula, such that the exposed portion of the cannula delivers ultrasonic energy at a frequency that is pre-selected to debride musculoskeletal tissue upon percutaneous insertion of the tip portion.

20 Claims, 7 Drawing Sheets

Related U.S. Application Data continuation of application No. 12/650,832, filed on Dec. 31, 2009.

(51) Int. Cl.
    *A61B 17/3205*      (2006.01)
    *A61B 90/20*      (2016.01)
    *A61B 90/00*      (2016.01)

(52) U.S. Cl.
    CPC ... *A61B 90/20* (2016.02); *A61B 2017/320084* (2013.01); *A61B 2090/378* (2016.02)

(56) References Cited

U.S. PATENT DOCUMENTS

| | | |
|---|---|---|
| 3,990,452 A | 11/1976 | Murry et al. |
| 4,188,952 A | 2/1980 | Loschilov et al. |
| 4,428,748 A | 1/1984 | Peyman |
| 4,515,583 A | 5/1985 | Sorich |
| 4,531,934 A | 7/1985 | Kossovsky et al. |
| 4,867,141 A | 9/1989 | Nakada et al. |
| 4,870,953 A | 10/1989 | Don Michael et al. |
| 4,920,954 A | 5/1990 | Alliger et al. |
| 5,038,756 A | 8/1991 | Kepley |
| 5,042,461 A | 8/1991 | Inoue et al. |
| 5,267,954 A | 12/1993 | Nita |
| 5,275,607 A | 1/1994 | Lo et al. |
| 5,344,395 A | 9/1994 | Whalen et al. |
| 5,413,556 A | 5/1995 | Whittingham |
| 5,417,654 A | 5/1995 | Kelman |
| 5,480,379 A | 1/1996 | La Rosa |
| 5,514,086 A | 5/1996 | Parisi et al. |
| 5,562,609 A | 10/1996 | Brumbach |
| 5,580,347 A | 12/1996 | Reimels |
| 5,626,563 A | 5/1997 | Dodge et al. |
| 5,814,016 A | 9/1998 | Valley et al. |
| 5,897,524 A | 4/1999 | Wortrich |
| 5,910,110 A | 6/1999 | Bastable |
| 5,911,700 A | 6/1999 | Mozsary et al. |
| D418,916 S | 1/2000 | Bastable |
| 6,033,375 A | 3/2000 | Brumbach |
| 6,077,285 A | 6/2000 | Boukhny |
| 6,102,046 A | 8/2000 | Weinstein et al. |
| 6,139,518 A | 10/2000 | Mozsary et al. |
| 6,206,014 B1 | 3/2001 | Cameron, III et al. |
| 6,214,017 B1 | 4/2001 | Stoddard et al. |
| 6,234,993 B1 | 5/2001 | Terpilowski et al. |
| 6,270,471 B1 | 8/2001 | Hechel et al. |
| 6,379,351 B1 | 4/2002 | Thapliyal et al. |
| 6,402,769 B1 | 6/2002 | Boukhny |
| 6,437,266 B1 | 8/2002 | Pannenborg et al. |
| 6,461,301 B2 | 10/2002 | Smith |
| 6,524,251 B2 | 2/2003 | Rabiner et al. |
| 6,551,337 B1 | 4/2003 | Rabiner et al. |
| 6,562,054 B1 | 5/2003 | Weber et al. |
| 6,623,444 B2 | 9/2003 | Babaev |
| 6,660,013 B2 | 12/2003 | Rabiner et al. |
| 6,695,781 B2 | 2/2004 | Rabiner et al. |
| 6,695,782 B2 | 2/2004 | Ranucci et al. |
| 6,964,647 B1 | 11/2005 | Babaev |
| 6,980,419 B2 | 12/2005 | Smith et al. |
| 7,077,820 B1 | 7/2006 | Kadziauskas et al. |
| 7,507,212 B2 | 3/2009 | Tsuchiya et al. |
| 7,845,235 B2 | 12/2010 | Sandu et al. |
| 7,850,707 B2 | 12/2010 | Yaguchi et al. |
| 3,025,672 A1 | 9/2011 | Novak et al. |
| 8,070,711 B2 | 12/2011 | Bassinger et al. |
| 8,075,503 B2 | 12/2011 | Jaeb |
| 8,303,505 B2 | 11/2012 | Webler et al. |
| 2002/0068930 A1 | 6/2002 | Tasto et al. |
| 2002/0107538 A1 | 8/2002 | Shibata et al. |
| 2002/0183720 A1 | 12/2002 | Hill et al. |
| 2004/0133168 A1 | 7/2004 | Salcudean et al. |
| 2004/0162546 A1 | 8/2004 | Liang et al. |
| 2004/0259483 A1 | 12/2004 | Newell |
| 2004/0267121 A1 | 12/2004 | Sarvazyan et al. |
| 2005/0101984 A1 | 5/2005 | Chanduszko et al. |
| 2005/0209621 A1 | 9/2005 | Gordon et al. |
| 2005/0228288 A1 | 10/2005 | Hurst |
| 2006/0195106 A1 | 8/2006 | Jones et al. |
| 2006/0241450 A1 | 10/2006 | Da Silva et al. |
| 2007/0250041 A1 | 10/2007 | Werp |
| 2007/0255196 A1 | 11/2007 | Wuchinich |
| 2007/0276352 A1 | 11/2007 | Crocker et al. |
| 2008/0004621 A1 | 1/2008 | Dahla et al. |
| 2008/0033349 A1 | 2/2008 | Suzuki |
| 2008/0033410 A1 | 2/2008 | Rastegar et al. |
| 2008/0058775 A1 | 3/2008 | Darian et al. |
| 2008/0195002 A1 | 8/2008 | Thompson et al. |
| 2008/0234710 A1 | 9/2008 | Neurohr et al. |
| 2009/0024076 A1 | 1/2009 | Babaev |
| 2009/0112098 A1 | 4/2009 | Vaezy et al. |
| 2009/0312693 A1 | 12/2009 | Thapliyal et al. |
| 2010/0056986 A1 | 3/2010 | Allen et al. |
| 2010/0076476 A1 | 3/2010 | To et al. |
| 2010/0211083 A1 | 8/2010 | Sauer |
| 2010/0312102 A1 | 12/2010 | Barnes et al. |
| 2011/0040212 A1 | 2/2011 | Dietz et al. |
| 2011/0160620 A1 | 6/2011 | Gill et al. |
| 2011/0251461 A1 | 10/2011 | Gonzalez et al. |
| 2012/0078164 A1 | 3/2012 | Mulvihill et al. |
| 2012/0083728 A1 | 4/2012 | Sorensen et al. |
| 2013/0331872 A1 | 12/2013 | Parham et al. |
| 2015/0039005 A1 | 2/2015 | Gill et al. |
| 2015/0351790 A1 | 12/2015 | Gill et al. |
| 2016/0059043 A1 | 3/2016 | Gill et al. |
| 2016/0096040 A1 | 4/2016 | Parham |

FOREIGN PATENT DOCUMENTS

| | | |
|---|---|---|
| CN | 2879983 Y | 3/2007 |
| CN | 101332340 A | 12/2008 |
| EP | 0709077 B1 | 3/2002 |
| EP | 1634542 A1 | 3/2006 |
| WO | 2007/143686 A2 | 12/2007 |
| WO | 2008/027223 A2 | 3/2008 |
| WO | 2008/040020 A2 | 4/2008 |
| WO | 2009/105628 A2 | 8/2009 |
| WO | 2012/019136 A2 | 2/2012 |
| WO | 2016/036810 A1 | 3/2016 |
| WO | 2016/054563 A1 | 4/2016 |

OTHER PUBLICATIONS

International Search Report and Written Opinion issued in PCT/US2009/034659, dated Oct. 1, 2009.

International Search Report and Written Opinion issued in PCT/US2010/062341, dated Mar. 25, 2011.

Kowalewski et al., Issues in Vacuum Brazing, May 1, 2006, available at https://www.secowarwick.com/assets/Documents/Articles/Vacuum-Furnaces/Issues-in-vacuum-brazing-VAC.pdf.

Lin et al., Clinical Outcomes of Ultrasound-Guided Aspiration and Lavage in Calcific Tendinosis of the Shoulder. HSSJ, 3:99-105 (2007), published online 2006.

Supplementary European Search Report Issued in EP Application No. 09712545, dated Jun. 20, 2011.

Supplementary European Search Report Issued in EP Application No. 09713554.5, dated Apr. 15, 2011.

International Search Report and Written Opinion dated Dec. 28, 2015 for International Application No. PCT/US2015/053812 filed on Oct. 2, 2015.

U.S. Appl. No. 14/710,478, filed May 12, 2015.

International Search Report and Written Opinion dated Nov. 27, 2015 for International Application No. PCT/US2015/048075 filed on Sep. 2, 2015.

Labanca et al., Piezoelectric surgery: twenty years of use. British Journal of Oral and Maxillofacial Surgery, 16:265-269 (2008).

Supplementary European Search Report Issued in EP Application No. 10841671, dated Sep. 5, 2016.

Maura Labanca et al., "Piezoelectric surgery: Twenty years of use," 46(4) British J Oral & Maxillofacial Surgery 265 (2008).

SYSTEM AND METHOD FOR MINIMALLY INVASIVE TISSUE TREATMENT USING ULTRASONIC CANNULA

CROSS-REFERENCE TO RELATED APPLICATIONS

This application is a continuation of U.S. application Ser. No. 14/514,262, filed Oct. 14, 2014, which is a continuation of U.S. application Ser. No. 12/650,832, filed Dec. 31, 2009. The contents of both applications are incorporated herein by reference.

BACKGROUND

Repetitive motion or use of particular body tissues can cause injuries or painful conditions to arise. For example, tennis elbow, or lateral epicondylalgia is a clinical syndrome in which patients experience pain at the lateral elbow. Such pain in the lateral elbow may be worsen over time and, despite adequate treatment, many patients develop chronic symptoms and eventually become candidates for surgical treatment.

A number of surgical procedures have been described to treat chronic lateral epicondylalgia. Particular open techniques typically require open surgical dissection down to the pathological tissue and therefore necessitate repair of the surgically compromised normal tissue. Some arthroscopic techniques can be slightly less invasive, but these arthroscopic elbow techniques have been associated with neurological complications and may require the use of a high-cost operating suite and associated personnel. Various percutaneous techniques have been described which release, ablate or resect the pathological tissue. These percutaneous techniques, however, generally require a noticeable skin incision, some surgical dissection, and the afore-mentioned use of a high-cost operating suite and supportive equipment and personnel.

SUMMARY

Some embodiments relate to a system for musculoskeletal tissue treatment under ultrasonic guidance. The system includes a delivery device and a controller adapted to deliver a power signal to the delivery device. The delivery device is adapted to deliver ultrasonic energy to musculoskeletal tissue and includes a housing portion, an ultrasound transducer, and a tip portion. The housing portion defines a compartment and has an aspiration conduit and an irrigation conduit. The ultrasound transducer is disposed in the compartment of the housing portion and is adapted to translate a power signal to ultrasonic energy. The tip portion is coupled to the housing portion and is adapted to deliver fluid coming through the irrigation conduit to a musculoskeletal tissue site and to deliver detritus coming from the musculoskeletal tissue site through the aspiration channel. The tip portion includes a cannula and a sleeve. The cannula has a proximal portion and a distal portion, where the cannula is coupled to the ultrasound transducer to receive ultrasonic energy from the ultrasound transducer and deliver the ultrasonic energy to the musculoskeletal tissue site. The sleeve is adapted for percutaneous insertion and forms a lumen receiving the proximal portion of the cannula.

Some embodiments relate to delivering ultrasonic energy to a target musculoskeletal tissue site. A delivery device is connected to a vacuum source, a fluid source, and a power signal source. The delivery device has a housing portion maintaining an ultrasound transducer and a tip portion having a sleeve and a cannula. The cannula is coupled to the ultrasound transducer and received in the sleeve to define a covered portion and an exposed portion. Ultrasonic energy is generated by sending a power signal from the power signal source to the ultrasound transducer. The ultrasonic energy is transmitted from the ultrasound transducer to the cannula, such that the exposed portion of the cannula delivers ultrasonic energy at a frequency that is pre-selected to debride musculoskeletal tissue upon percutaneous insertion of the tip portion.

While multiple embodiments are disclosed, still other embodiments will become apparent to those skilled in the art from the following detailed description, which shows and describes various examples for understanding. Accordingly, the drawings and detailed description are to be regarded as illustrative in nature and not restrictive.

While the inventive aspects are amenable to various modifications and alternative forms, embodiments have been shown by way of example in the drawings and are described in detail below. The intention, however, is not to limit the inventive aspects to the particular embodiments shown and described. On the contrary, the invention is intended to cover all modifications, equivalents, and alternatives falling within the scope of invention as defined by the appended claims.

DETAILED DESCRIPTION

Various embodiments described herein provide systems for accessing and treating target body tissue (e.g., tendon tissue, ligament tissue, muscle tissue, bony tissue, and the like) under guidance of ultrasound imaging equipment. In some embodiments, the system includes a delivery device that is pre-tuned to an ultrasonic energy frequency range selected for debridement of pathologic musculoskeletal tissue. According to some embodiments, the delivery device, also termed a hand piece, includes echogenic material and/or etching to facilitate ultrasonic imaging and is adapted for percutaneous insertion without producing a noticeable skin incision. Portions of the system, including the delivery device and associated tubing set, are optionally adapted to be discarded after a single use.

In some implementations, a high-frequency ultrasound transducer and associated ultrasound imaging equipment provide visual detail of the tendinopathic changes of lateral epicondylalgia, so pathologic tissue is better identified at the time of a procedure without the need to cut the skin. Thereafter, pathologic tissue or other target tissue is accessible and treatable using the system without a noticeable skin incision. One procedure includes an ultrasound-guided percutaneous tenotomy for chronic lateral epicondylalgia, where the use of ultrasound equipment and echogenic instrumentation helps provide precise localization and treatment of the pathological tissue under real-time guidance while minimizing trauma to non-affected tissues. Other tissues in the elbow joint and in other parts of the body are contemplated for treatment using systems described herein. Also, in some embodiments, systems additionally or alternatively serve to deliver therapeutic agents to the site before or after tissue is treated or are used to accomplish a variety of tissue treatments (e.g., tissue disruption, debridement, decortication, or others).

Figure 1:
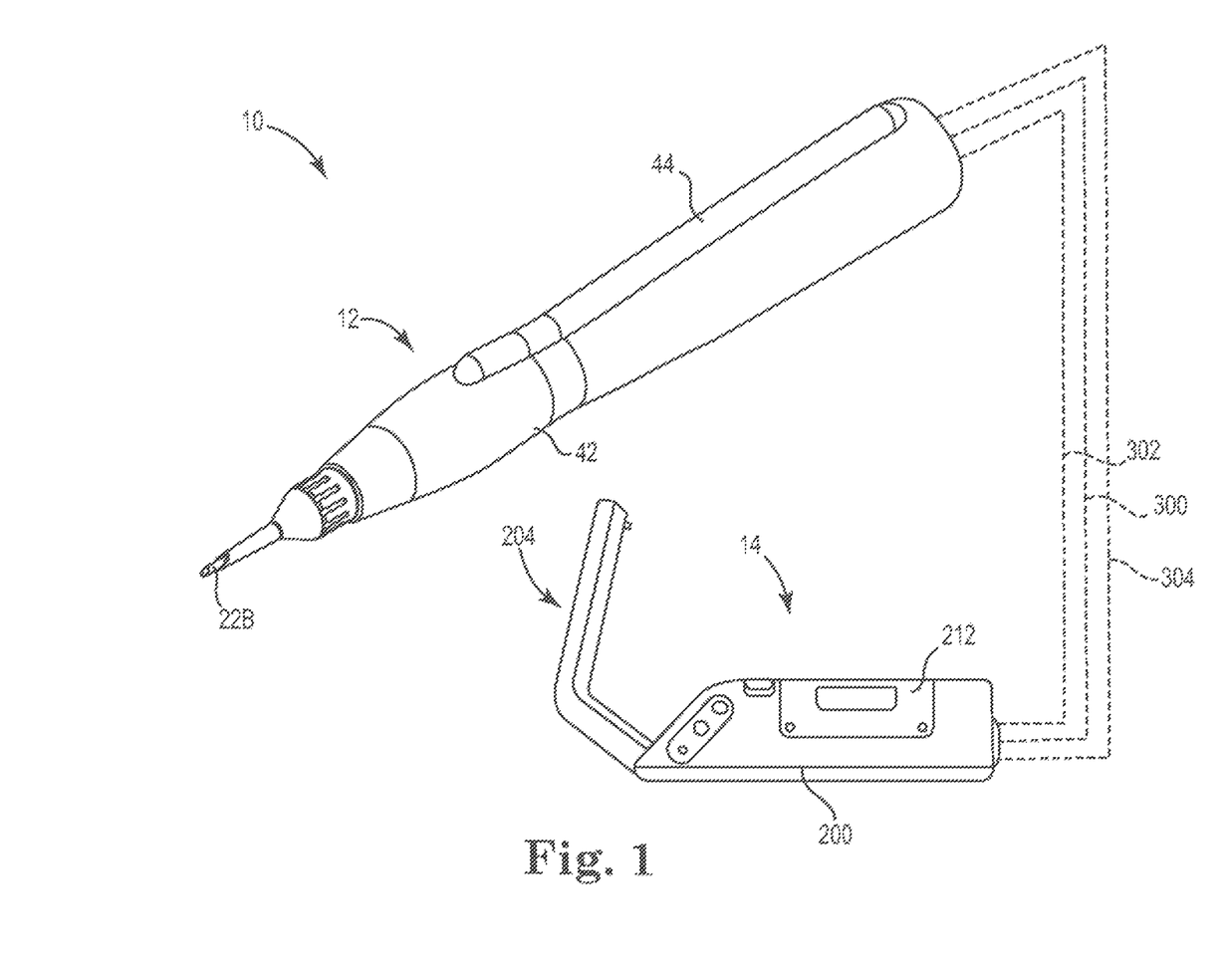
FIG. 1 shows a system for accessing and treating tissue, according to some embodiments.

FIG. 1 shows a system 10 for percutaneously accessing and acting upon target tissue while helping reduce collateral trauma, according to some embodiments. In some embodiments, the percutaneous, minimally-invasive nature of the system 10 facilitates treatment of a patient in an office setting under local anesthesia. Treatment in an office setting is advantageous in several respects, including patient comfort and convenience and avoiding costs associated with operating room time and general anesthesia, for example. The system 10 includes a delivery device 12 adapted to deliver ultrasonic energy to musculoskeletal tissue and a controller 14 connected to the delivery device 12 (e.g., via wired communication, wireless communication, or combinations thereof). Generally, various components of the delivery device 12 contemplated for tissue contact are formed of biocompatible and/or other suitable materials depending upon implementation.

Figure 2:
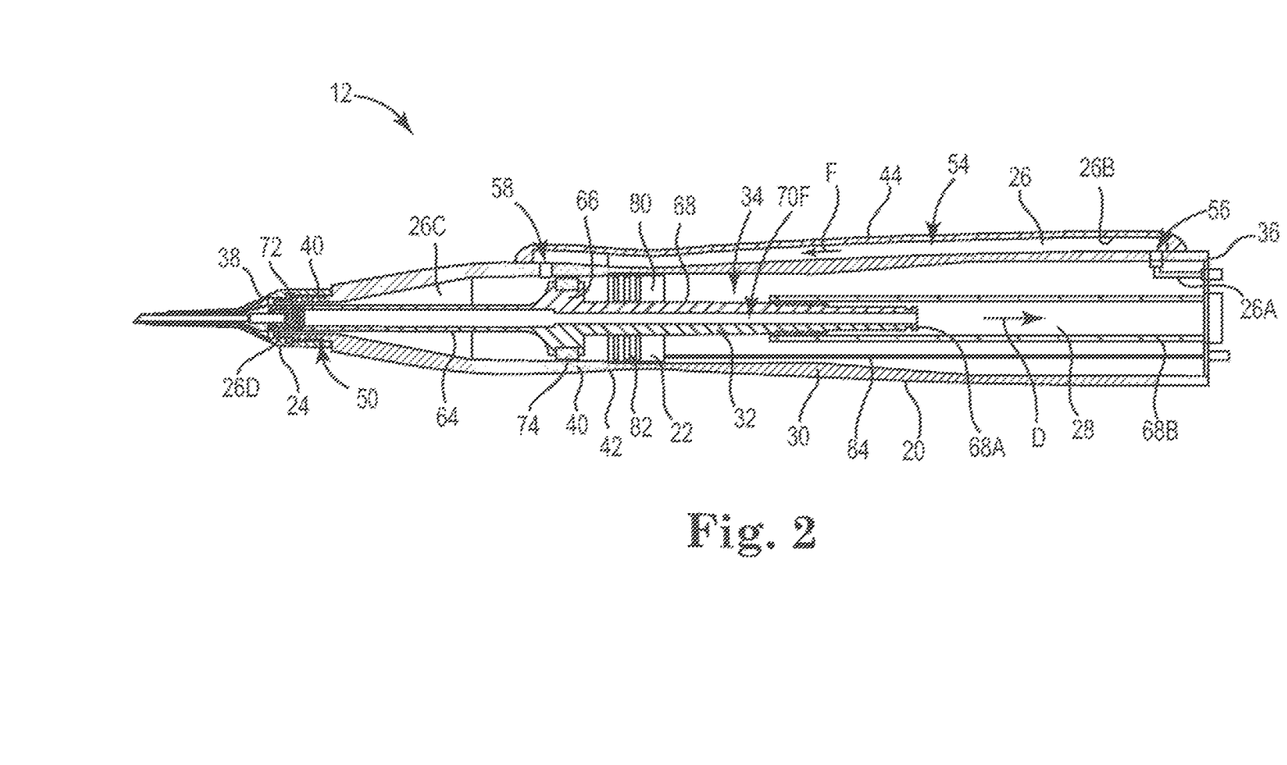
FIG. 2 is a longitudinal section of a delivery device of the system of FIG. 1, according to some embodiments.

As shown in FIG. 1, the delivery device 12, also described as a hand piece, is optionally ergonomically designed, adapted to be hand held (e.g., as a stylet) or otherwise adapted to be manually operated using a single hand. In other implementations, the delivery device 12 is adapted to be manipulated automatically or semi-automatically (e.g., as part of a robotic system). FIG. 2 shows a longitudinal section of the delivery device 12, according to some embodiments. As shown in FIG. 2, the delivery device 12 includes a housing portion 20, an ultrasound transducer 22 maintained within the housing portion 20, and a tip portion 24 that is removably coupled to the housing portion 20, according to some embodiments.

In some embodiments, the housing portion 20 provides means for maintaining the transducer 22 and forms an irrigation conduit 26 and a vacuum conduit 28, where the housing portion 20 includes a body 30 and a mounting post 32 received in the body 30. As illustrated, portions of the irrigation and vacuum conduits 26, 28 are formed by the body 30 and mounting post 32. The body 30 defines an inner compartment 34 and extends from a proximal end 36 to a distal end 38, the body 30 forming a nose portion 40 toward the distal end 38, a grip portion 42 proximal from the nose portion 40, and a fluid bypass 44 separated from and extending adjacent to the inner compartment 34. In some embodiments, the body 30 is formed of Acrylonitrile Butadiene Styrene, although a variety of materials are contemplated.

As shown, the inner compartment 34 is generally an elongate space within the body 30, extending through the grip portion 42 distally through the nose portion 40. In some embodiments, the inner compartment 34 is adapted to receive the ultrasound transducer 22 and the mounting post 32, as well as any other incorporated components (e.g., a power signal source such as a battery and control circuitry, or other features) and forms a part of the irrigation conduit 26 in combination with the mounting post 32 as subsequently described.

In some embodiments, the nose portion 40 is generally narrowed in diameter relative to the grip portion 42. As shown, the nose portion 40 optionally includes external threading 50 for releasably mating with the tip portion 24.

In some embodiments, the grip portion 42 includes a contoured profile to enhance grip and facilitate manual control of the device 12 by a user. As shown, the fluid bypass 44 extends along an external portion of the grip portion 42 according to some implementations, where the fluid bypass 44 defines a hollow lumen 54 having an inlet 56 from the inner compartment 34 near the proximal end 36 of the body 30 and an outlet 58 back into the inner compartment 34. As subsequently described, the fluid bypass 44 also forms a portion of the irrigation conduit 26.

In some embodiments, the mounting post 32 includes a neck 64, a collar 66, and a stem 68 and defines an inner lumen 70 which forms a portion of the vacuum conduit 28. The neck 64 is elongate and tubular and includes internal threading 72 within the inner lumen 70. The collar 66 has a relatively larger diameter than the neck 64 and resides intermediate the neck 64 and stem 68, where the neck 64 extends distally from the collar 66 and the stem 68 extends proximally from the collar 66. As shown, the collar 66 optionally includes a gasket 74, or O-ring, for forming a fluid seal with the inner compartment 34 of the body 30 proximal to the outlet 58 of the fluid bypass 44. The stem 68 has a relatively smaller diameter than the collar 66 and is adapted to coaxially receive the ultrasound transducer 22 according to some embodiments. In order to facilitate assembly, the stem 68 is optionally formed of first and second tubular members 68A, 68B coupled via complementary threading and/or a frictional fit, for example.

In some embodiments, the neck 64, the collar 66, and the first tubular member 68A of the stem 68 are formed of a material that is suitable for conveying ultrasonic energy. For example the neck 64, collar 66, and the first tubular member 68A are optionally formed of a stainless steel alloy, although a variety of materials are contemplated. In some embodiments, the second tubular member 68B of the stem 68A is formed of a dampening or insulating material, such as a relatively soft polymeric material, for reducing or inhibiting proximal transmission of ultrasonic energy or other undesirable ultrasonic energy transmission. For example the second tubular member 68B is optionally formed of polytetrafluoroethylene, although a variety of materials are contemplated.

The ultrasound transducer 22, or transducer 22, is maintained in the inner compartment 34 of the housing portion 20 by the mounting post 32 and provides means for generating ultrasonic energy from a power signal. The ultrasonic energy is optionally applied in a pulsed fashion or continuous fashion as desired. The transducer 22 optionally takes a variety of forms, but according to some embodiments includes an enclosure 80 housing a plurality of piezoelectric crystals 82 and electrodes and a power conduit 84 for carrying a power signal to the transducer 22. In particular, the transducer 22 is adapted to translate a power signal from the controller 14 to ultrasonic energy. The enclosure 80 of the transducer 22 is mounted to first tubular member 68A of the stem 68 such that ultrasonic energy generated by the transducer 22 is conveyed into and through the mounting post 32 distally to the neck 64 of the mounting post 32. The transducer 22 is optionally adapted to generate longitudinal vibration, transverse vibration, or combinations thereof at desired frequencies. For example, the number and configuration of the piezoelectric crystals 82 are optionally varied to modify the ultrasonic frequency used for tissue treatment.

With the transducer 22 secured coaxially about the mounting post 32, the inner lumen 70, and thus the vacuum conduit 28, pass through the transducer 22. As shown in FIG. 2, the vacuum conduit 28 is generally formed by the mounting post 32, where the inner lumen 70 of the mounting post 32 provides an aspiration duct through the housing portion 20. To facilitate assembly of the system 10, the second tubular member 68B is optionally secured to the proximal end 36 of the body 30 and capped with a connector as desired. In some embodiments, the second tubular member 68B is configured to include a removable filter and/or a collection container for collecting and filtering detritus from the target site.

As shown, the irrigation conduit 26 is formed by a combination of the body 30 and mounting post 32 of the housing portion 20. In some embodiments, assembly of the housing portion 20 and the mounting post 32 includes coaxially receiving the mounting post 32 within the inner compartment 34 of the body 30 such that the gasket 74 engages the body 30 proximal to the outlet 58 of the fluid bypass 44. The mounting post 32 is optionally frictionally fit, adhered, welded, or otherwise secured within the body 30 according to various embodiments. The power conduit 84 of the transducer 22 is extended distally from the enclosure 80, secured to the proximal end 36 of the body 30, and is optionally capped with a connector as desired.

The irrigation conduit 26 is defined by a first portion 26A, a second portion 26B, a third portion 26C, and a fourth portion 26D. The first portion 26A optionally includes a tubular connector secured to the body 30 at the proximal end 36 and coupled to the inlet 56 of the fluid bypass 44. The second portion 26B includes the fluid bypass 44. The third portion 26C includes a portion of the inner compartment 34 between the neck 64 of the mounting post 32 and the body 30 that is distal to the collar 66 of the mounting post 32 and proximal to the nose portion 40 of the body 30. The fourth portion 26D includes a part of the inner compartment 34 between the nose portion 40 of the body 30 and the neck 64 of the mounting post 32. Thus, fluid flow F passing into the irrigation conduit 28 in a distal direction passes sequentially through the first, second, third, and fourth portions 26A, 26B, 26C, 26D with fluid encircling, or circumscribing the neck 64 of the mounting post 32.

In some embodiments, the tip portion 24 is adapted to be coupled to the housing portion 20, deliver fluid coming through the irrigation conduit 26 to a target site, deliver detritus flow D coming from the target site into the vacuum conduit 28, and deliver ultrasonic energy from the transducer 22 (conveyed via the mounting post 32) to the target site. As subsequently described in greater detail, in some embodiments, the tip portion 24 provides means for transmitting the ultrasonic energy to a percutaneous musculoskeletal site at a pre-tuned frequency selected to debride musculoskeletal tissue.

Figure 3:
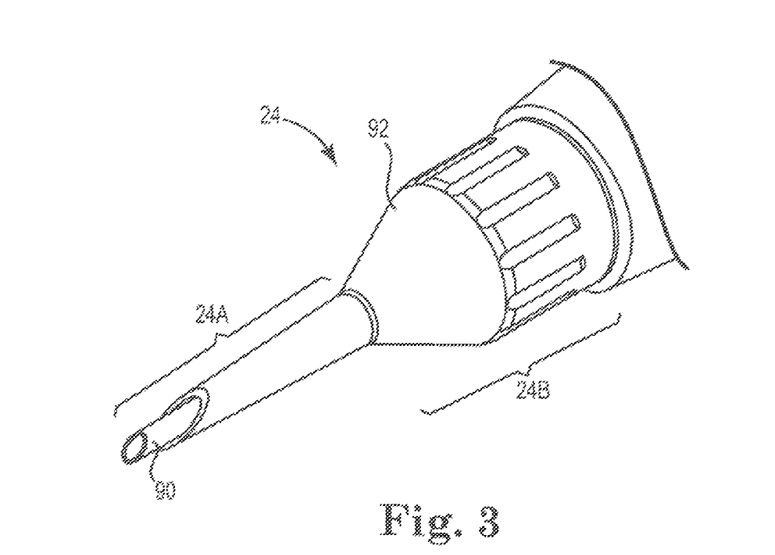
FIG. 3 is an enlarged perspective view of a tip portion of the delivery device of FIG. 1, according to some embodiments.
Figure 4:
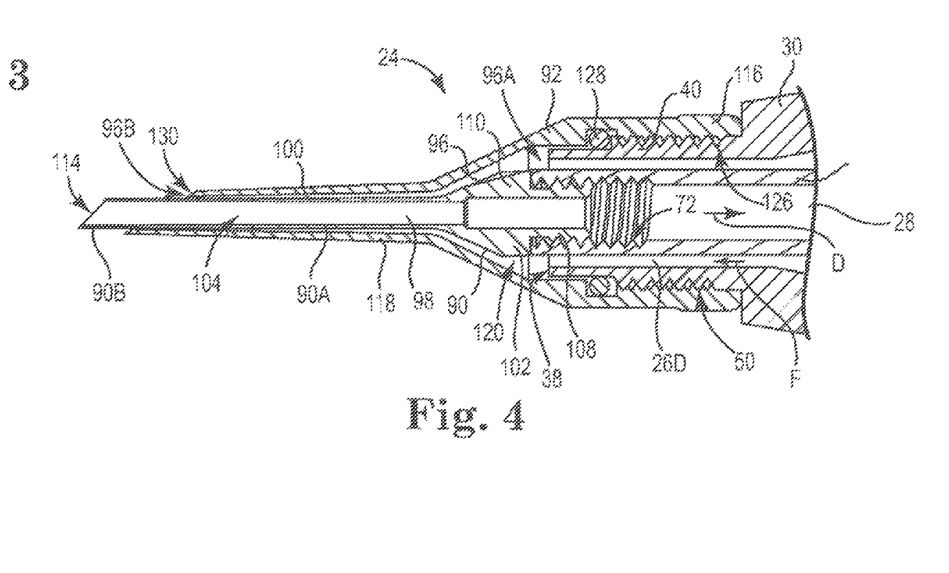
FIG. 4 is a longitudinal section of the view of FIG. 3, according to some embodiments.

FIG. 3 is an enlarged isometric view of the tip portion 24 with the body portion 22 of the device 12 being largely cut away and FIG. 4 is a longitudinal section of the view of FIG. 3, according to some embodiments. As shown in FIG. 3, the tip portion 24 defines a distal section 24A adapted for percutaneous insertion without having to form an incision in the skin and a proximal section 24B adapted for coupling to the housing portion 20.

As shown in FIG. 4, the tip portion 24 includes a cannula 90 and a sleeve 92 covering a section of the cannula 90 to define a covered portion 90A and an exposed portion 90B of the cannula 90. The tip portion 24 also defines an irrigation conduit 96 and a vacuum conduit 98. In some embodiments the cannula 90 is a generally hollow tubular member having a distal, insertion portion 100 and a proximal, coupling portion 102. The cannula 90 also defines an inner lumen 104 extending longitudinally through the insertion and coupling portions 100, 102. In some embodiments, the cannula 90 is formed of an echogenic, biocompatible material suitable for conveying ultrasonic energy. For example, the cannula 90 is optionally formed of a stainless steel alloy according to various embodiments. In other embodiments, the cannula 90 is covered or coated with echogenic material.

In some embodiments, the coupling portion 102 of the cannula 90 includes a threaded base 108 and a flange 110 extending distally from the threaded base 108. The threaded base 108 is adapted to mate with the internal threading 72 of the mounting post 32 with the flange 110 abutting the mounting post 32. The flange 110 has a relatively larger diameter than the threaded base 108 and necks down in diameter to transition to the insertion portion 100. The insertion portion 100 of the cannula 90 extends smoothly from the coupling portion 102 of the cannula 90 to a terminal end 114 and is adapted for percutaneous insertion.

In some embodiments, the terminal end 114 of the insertion portion 100 is formed at a sharp angle or in other embodiments is simply squared off (not shown). Additionally, the insertion portion 100 optionally includes serrated edges or other surface features (not shown) for enhancing ultrasonic debridement.

In some embodiments, the insertion portion 100 of the cannula 90 has a size of about 12 gauge or less, about 12 gauge to about 25 gauge, or about 14 gauge to about 22 gauge, for example. In some embodiments, the insertion portion 100 has a lateral width of about 2.5 mm or less, about 2.2 mm to about 0.4 mm, or about 2.1 mm to about 0.5 mm, for example. In some embodiments, the length of the insertion portion 100 is about 3.0 inches to about 0.25 inches, about 2.7 inches to about 0.5 inches, or about 2.5 inches to about 1.0 inch, for example. Although some examples are provided herein which facilitate percutaneous insertion, other dimensions are also contemplated.

As shown in FIG. 4, the sleeve 92 is a generally hollow tubular member adapted to extend over the covered portion 90B of the cannula 90. In some embodiments, the sleeve 92 reduces unwanted, collateral transmission of heat, ultrasonic energy, or other byproducts of the ultrasonic energy being conveyed along the covered portion 90B of the cannula 90 and also helps provide a path for irrigation fluid to the exposed portion 90A of the cannula 90. According to some embodiments, the sleeve 92 reduces or eliminates damage to non-target body tissues as a result of unwanted transmission of ultrasonic energy.

Similarly to the cannula 90, the sleeve 92 has a proximal, coupling portion 116 and a distal, insertion portion 118 extending from the coupling portion 116 and defining an inner lumen 120. The sleeve 92 or a portion thereof is optionally formed of an echogenic, biocompatible material suitable for dampening products of ultrasonic energy (e.g., heat and vibration). In other embodiments, the sleeve 92 is coated with an echogenic material. In some implementations, the sleeve 92 is formed of a material exhibiting a differential echogenicity to that of the cannula 90. In such embodiments, both the cannula 90 and sleeve 92 facilitate ultrasonic imaging and separate identification during percutaneous insertion. For example, in some embodiments the sleeve 92 is formed of an echogenic polytetrafluoroethylene, although other materials are contemplated.

As shown, the coupling portion 116 of the sleeve 92 includes internal threading 126 adapted to mate with nose portion 40 of the body 30 and necks down in diameter to transition to the insertion portion 118 of the sleeve 92. The coupling portion 116 also includes a gasket 128 or O-ring for forming a fluid seal with the nose portion 40. The insertion portion 118 of the sleeve 92 extends smoothly from the coupling portion 116 to a terminal end 130 and is adapted for percutaneous insertion.

The terminal end 130 of the insertion portion 118 is optionally formed with a sharp angle or in other embodiments is simply squared off (not shown). In some embodiments, the insertion portion 118 is adapted to leave the exposed portion 90B of the cannula 90 a length of about 10 mm or less, for example between from 2 mm to about 10 mm, although a variety of dimensions are contemplated.

In some embodiments, and depending upon the size of the cannula 90 as the sleeve 92 receives the cannula 90, the insertion portion 118 of the sleeve 92 has a size of about 12 gauge or less, about 12 gauge to about 25 gauge, or about 14 gauge to about 22 gauge, for example. In some embodiments, the insertion portion 118 has a lateral width of about 2.5 mm or less, about 2.2 mm to about 0.4 mm, or about 2.1 mm to about 0.5 mm, for example. In some embodiments, the length of the insertion portion 118 is about 3.0 inches to about 0.25 inches, about 2.7 inches to about 0.5 inches, or about 2.5 inches to about 1.0 inch, for example. Although some examples are provided herein which facilitate percutaneous insertion, other dimensions are also contemplated.

As shown in FIG. 4, the vacuum conduit 98 is generally formed by the cannula 90, where the inner lumen 104 of the cannula 90 provides an aspiration duct through the tip portion 24 with an inlet at the terminal end 114 of the cannula 90. In turn, the irrigation conduit 96 is formed upon securing the cannula 90 and the sleeve 92 relative to one another. In some embodiments, the cannula 90 and sleeve 92 are separately secured to the housing portion 20 of the delivery device 12 and do not contact one another. Once the cannula 90 and the sleeve 92 are secured relative to one another, with the cannula received in the inner lumen 120 of the sleeve 92, the cannula 90 and the sleeve 92 define a gap between them to form the irrigation conduit 96 of the tip portion 24, with an inlet 96A into the irrigation conduit 96 being defined between the coupling portions 100, 116 of the cannula 90 and the sleeve 92, the inlet 96A being positioned distal to the gasket 128. An outlet from the irrigation conduit 96B is defined between the terminal end 130 of the sleeve 92 and the cannula 90. Thus, fluid F passing into the irrigation conduit 96 in a distal direction passes from the irrigation conduit 26 into the inlet 96A and out from the outlet 96B with fluid generally encircling, or circumscribing the insertion portion 100 of the cannula 90 and being directed toward the exposed portion 90B of the cannula 90.

In some embodiments, assembly of the delivery device 12 includes removably securing the tip portion 24 to the housing portion by screwing the tip portion 24 onto the housing portion 20 with the coupling portion 102 of the cannula 90 coming into close contact with the neck 64 of the mounting post 32 such that ultrasonic energy generated by the transducer 22 is transferred from the mounting post 32 to the cannula 90 and vacuum is able to be pulled through the vacuum conduits 28, 98. Also, the gasket 74 of the tip portion 24 seals sleeve 92 to the nose portion 40 such that fluid is able to be delivered through the irrigation conduits 26, 96.

As previously referenced, in some embodiments, the insertion portions 100, 118 of the tip portion 24 help facilitate atraumatic skin and soft tissue penetration—also described as percutaneous access without a need for a separate incision—under ultrasonic imaging. Moreover, in some embodiments, the delivery device 12 is pre-tuned to a selected ultrasonic energy frequency or frequency range. For example, it has surprisingly been found that an ultrasonic energy frequency range from about 25 kHz to about 29 kHz effectively debrides pathologic musculoskeletal tissue (e.g., scar tissue associated with a tendon) while reducing the likelihood of trauma to healthy soft tissue. Various features of the delivery device 12 influence the ultrasonic energy frequency being delivered from the exposed portion 90B of the cannula 90, including size, shape, and material of the mounting post 32, size, shape, and material of the cannula 90, and configuration of the transducer 22 (including size, shape, and number of piezoelectric crystals, for example).

Figure 5:
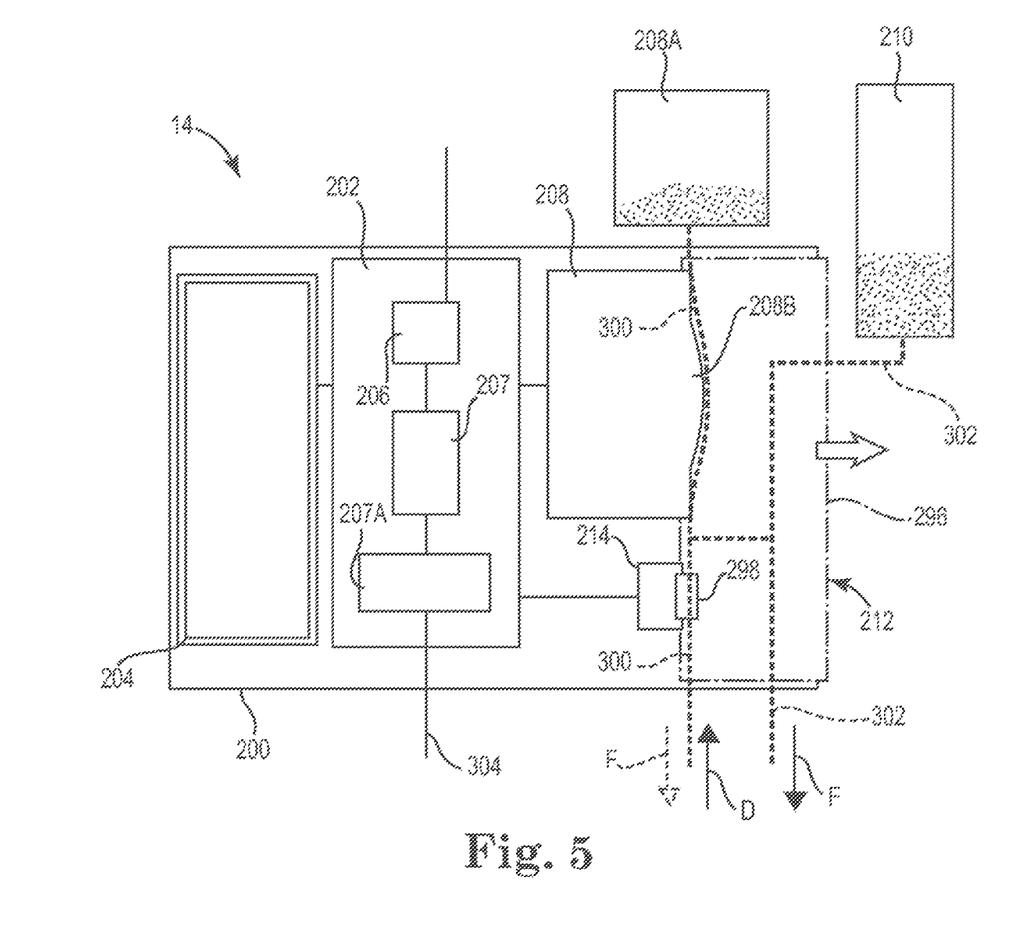
FIG. 5 is a schematic view of a controller of the system of FIG. 1, according to some embodiments.

FIG. 5 is a schematic view of the controller 14, according to some embodiments. As shown, the controller 14 includes a housing 200; a command module 202 including a user interface 204, a power source 206, and a processor 207; a vacuum source 208; an irrigation source 210; and a tubing cassette 212.

The housing 200 is generally shown in FIG. 1 and serves to house the various components and provide connector ports, for example. The command module 202 is adapted to control flow from the vacuum source 208, control flow from the irrigation source 210, power the delivery device 12, and send and receive instructions to and from a user via the user interface 204, where the processor 207 of the command module 202 includes software and hardware (e.g., ASIC or general purposes ICs, memory, ports, etc.) for providing means to generate and deliver a power signal to the delivery device 12. In some embodiments, the command module 202 includes signal filter means 207A for delivering a conditioned power signal (e.g., a sinusoidal power signal at a selected amplitude and frequency) to the delivery device 12.

In some embodiments, the user interface 204 includes a touch screen system and provides a means for controlling the system 10 via a sequentially-oriented operation process as will be subsequently described. The power source 206 optionally includes a battery, a capacitor, a transformer connected to an external power source, such as a wall socket, combinations thereof, or other means for providing electrical power to the system 10. As generally illustrated, in some embodiments, the power source 206 directly or indirectly delivers power to the various components of the controller 14 as appropriate.

As shown, the vacuum source 208 is optionally a vacuum pump (e.g., a peristaltic pump) disposed within the housing 200, though in other embodiments the vacuum source 208 is a connection to an external vacuum source (e.g, "house" vacuum), or other source for providing vacuum or aspiration flow D. The controller 14 also optionally includes a collection container 208A for receiving detritus, fluid, or other matter being aspirated by the aspiration flow D. The irrigation source 210 includes a reservoir of irrigant (e.g., saline) that is pressurized by gravity, a plunger (e.g., a syringe), or a pump (e.g., a peristaltic pump operated by the controller 14 and optionally disposed within the housing 200) to generate fluid flow F. The controller 14 also optionally includes a valve actuator 214 for directing fluid flow F into the vacuum conduits 28, 98 of the delivery device 12, for example to for flushing purposes.

Figure 6:
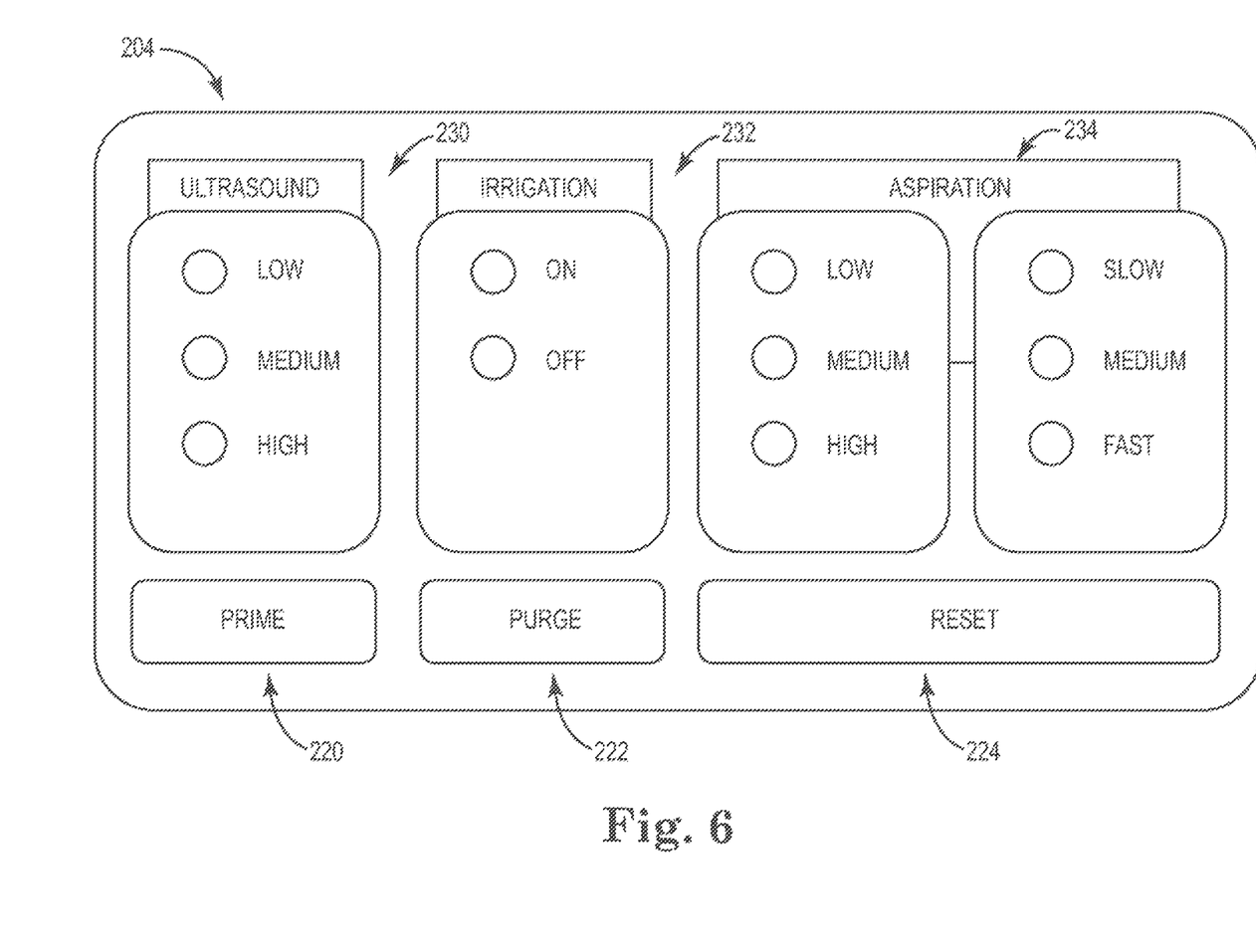
FIG. 6 is a schematic view of a user interface of the controller of FIG. 5, according to some embodiments.

FIG. 6 shows a display of the user interface 204. In operation, the user interface 204 provides a user (not shown) an intuitive sequence for operating the system 10 as will be described in greater detail below. As shown, the user interface 204 includes a prime phase 220, a purge phase 222, and a reset phase 224 and allows sequential operation of the delivery device 12 starting with an ultrasound level selection 230, an irrigation level selection 232, and an aspiration level selection 234, where a user is allowed to first select the ultrasound level 230, then the irrigation level 232, and finally the aspiration level 234 in sequence when operating the system 10. In some embodiments, the selections 230, 232, 234 are illuminated sequentially, first with the ultrasound level selection 230, and a user is not allowed to make a subsequent selection until the selection at hand has been made. In some methods of operation, the ultrasound energy and irrigant, or fluid flow, are generally delivered concurrently, while aspiration flow is delivered intermittently. For example, the ultrasound energy and irrigant flow optionally cease during aspiration and are restarted once treatment is reinitiated. Alternatively, irrigant flow ceases and ultrasound energy continues during aspiration, although some of the beneficial effects from using irrigant during ultrasonic treatment (e.g., continuous tip cooling and tissue emulsification, as well as others) are potentially reduced by such operation.

As indicated by the block arrow in FIG. 5, the tubing cassette 212 is removable from the housing 200 and includes a housing 296, a valve 298, a vacuum line 300, and an irrigation line 302 (designated by broken lines) maintained by the housing 296, the vacuum and irrigation lines 300, 302 providing connections between the vacuum source 208 and the delivery device 12 and between the irrigation source 210 and the delivery device 12. The vacuum line 300 is also optionally connected to the collection container 208A as previously referenced. In some embodiments, the vacuum and irrigation lines 300, 302 include a plurality of interconnected segments of medical tubing, although unitary constructs are a potential option as well. Although the collection container 208A is shown generally separate from the cassette 212, in some embodiments the collection container 208A is maintained by, formed as a part of, or is a component within the cassette 212. In some embodiments, the cassette 212 provides means for connecting the vacuum line 300 to the vacuum source 208 in a relatively sterile manner. For example, where the vacuum source 208 includes a peristaltic pump, the cassette 212 includes a seat structure 296A for causing the vacuum line 300 to engage a pump drive 208B of the vacuum source 208 that generates aspiration flow in the vacuum line 300.

Figure 7A:
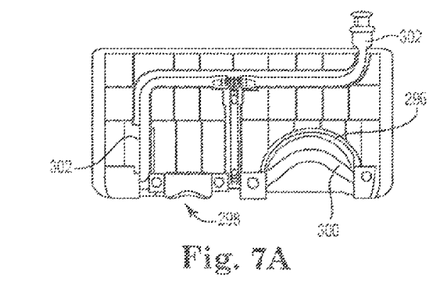
FIGS. 7A, 7B, and 7C show a tubing cassette of the controller of FIG. 5, according to some embodiments.
Figure 7B:
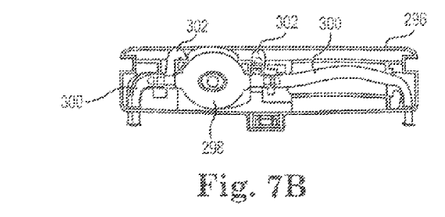
Figure 7C:
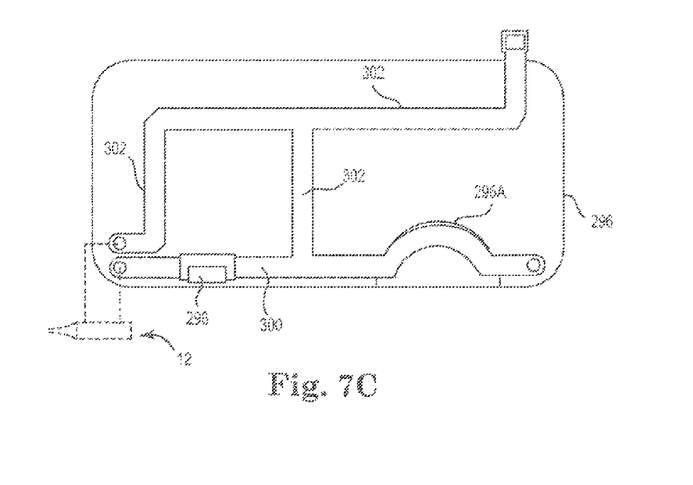

FIG. 7A shows an interior side of the tubing cassette 212 and FIG. 7B shows a bottom side of the tubing cassette 212, according to some embodiments. FIG. 7C is a schematic view of the tubing cassette 212, according to some embodiments. As previously described, the tubing cassette 212 includes a housing 296, a seat structure 296A, a valve 298, a vacuum line 300, and an irrigation line 302 (the vacuum and irrigation lines 300, 302 optionally being collectively referred to as a tubing set). In operation, the pump drive 208B (FIG. 5) of the vacuum source 208 (e.g., a peristaltic pump) is received in the seat structure 296A such that the vacuum line 300 is engaged against the seat structure 296A between the pump drive 208B and the seat structure 296A. The valve 298 is engaged by the valve actuator 214 to press the valve 298 closed such that flow from the irrigation line 302 will not travel through the vacuum line 300 to the delivery device 12 (designated generally by a broken line rectangle in FIG. 7C). When the vacuum line 300 is to be flushed, for example, the valve 298 is released and fluid is able to flow into the vacuum line 300 to the device and through the vacuum conduits 28, 98. As previously referenced, the irrigant flowing through the irrigation line 302 is optionally gravity pressurized or otherwise forced through the system 10.

Examples of additional or alternative system features and implementations, including alternate drive mechanism, working tip, and controller features as well as various treatment procedures are provided in PCT International Application No. PCT/US2009/034659, published on Aug. 27, 2009, having an international filing date of Feb. 20, 2009, and entitled "Systems, Devices and Methods for Accessing Body Tissue," the contents of which are incorporated herein by reference in their entirety. For example, in some embodiments, the housing portion 20 of the delivery device 12 includes or is connectable to one or more complementary working instruments (not shown), such as a trocar or percutaneous imaging head.

Assembly of the system 10 includes remotely connecting the delivery device 12 to the controller 14, where the controller 14 is a separate, remote module from the delivery device 12. In other embodiments, the delivery device 12 and the controller 14, or portions thereof, are formed as a single unit.

As indicated in FIGS. 1 and 5, a power line 304 is used to remotely connect the controller 14 to the power conduit 84 (FIG. 2) of the transducer 22 such that the controller 14 is able to supply a power signal to the delivery device 14. The tubing cassette 212 is removably coupled to the housing 200 of the controller 14 and the vacuum line 300 is connected to the vacuum conduit 28 (FIG. 2) and the irrigation line 302 is connected to the irrigation source 210 (FIG. 2). A user (not shown) is then manipulates the delivery device 12 under ultrasonic guidance and control delivery of ultrasonic energy, fluid flow, and vacuum flow using the interface 204 of the controller 14, according to some embodiment.

Figure 8:
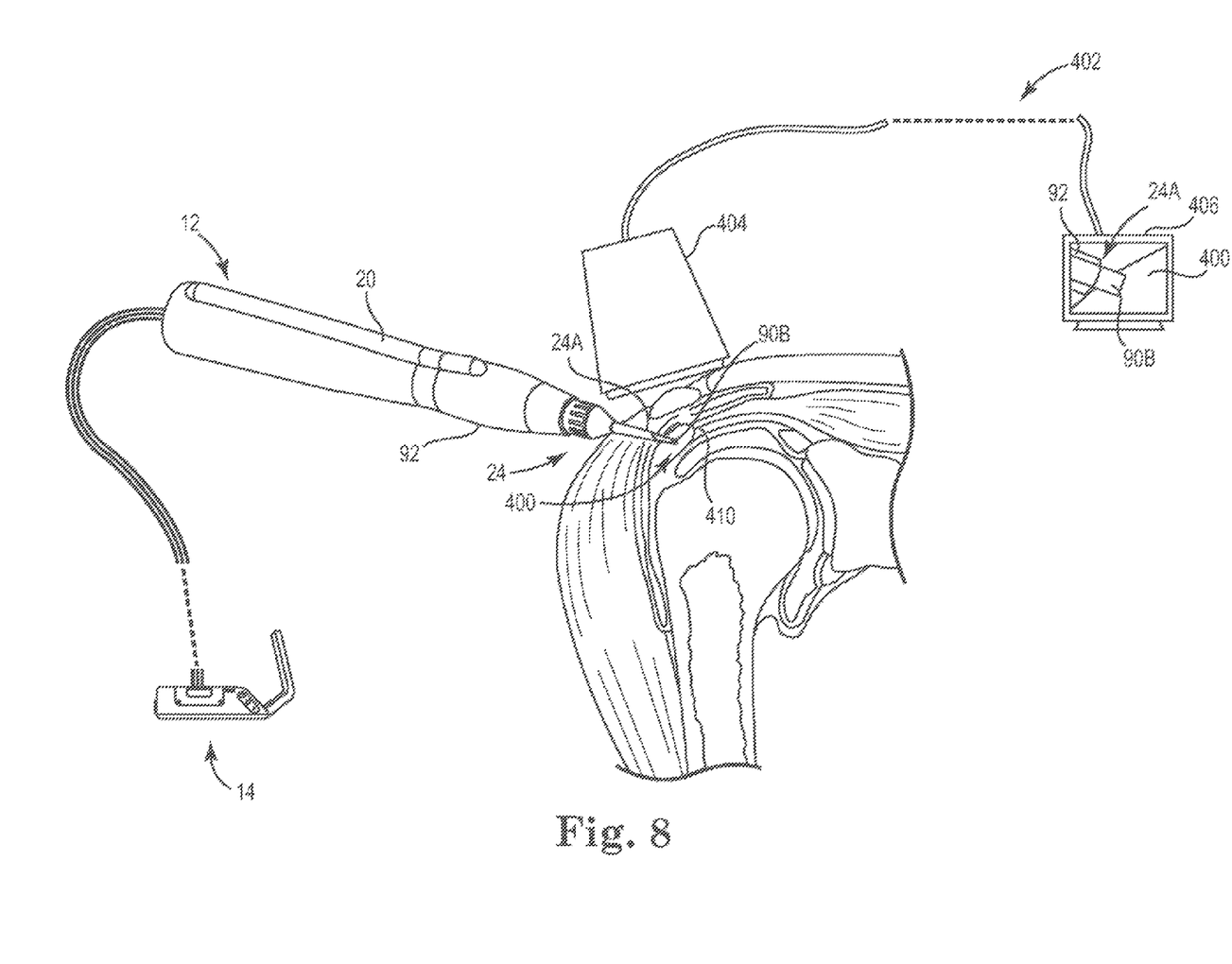
FIG. 8 shows a tenotomy procedure using the system of FIG. 1 under ultrasonic guidance, according to some embodiments.

FIG. 8 illustrates a method of delivering ultrasonic energy to a target musculoskeletal tissue site under ultrasonic imaging. As previously referenced, in some embodiments, the distal section 24A (FIG. 2) of the tip portion 24 is adapted to penetrate the skin and soft tissue, thereby facilitating percutaneous access to target musculoskeletal tissue site.

As shown in FIG. 8, advancement of the distal section 24A of the tip portion 24 to a target musculoskeletal tissue site 400 is optionally performed under guidance of an ultrasound imaging system 402 including a high-frequency ultrasound transducer 404 (e.g., a frequency greater than about 10 MHz) and an imaging device 406. The imaging system 402, in combination with the echogenic nature of the tip portion 24, permits intra-operative identification of the target tissue site 400 in need of treatment and an ability to percutaneously deliver ultrasonic energy from the exposed portion 90A of the cannula 90 to the target tissue site 400.

Some methods of delivering ultrasonic energy to the target tissue site 400 include connecting the delivery device 12 to the vacuum source 208, the irrigation source 210, and the power source 206 of the controller 14 (directly or via the command module 202). Ultrasonic energy is generated by sending a power signal from the command module 202 to the ultrasound transducer 22. The ultrasonic energy is transmitted from the ultrasound transducer 22 to the cannula 90, such that the exposed portion 90B of the cannula 90 delivers ultrasonic energy at a frequency that is pre-selected to debride musculoskeletal tissue upon percutaneous insertion of the distal section 24A of the tip portion 24 to the target musculoskeletal tissue site 400.

As referenced, the user interface 204 is optionally operated by a user to sequentially start up the delivery device 12, including initiating ultrasonic energy delivery, irrigation flow to the device 12, and aspiration flow from the device 12. Once tissue treatment is completed, according some embodiments, the tubing cassette 212 is removed from the controller 14, discarded, and replaced with a second, sterile tubing cassette (not shown) and is either pre-connected or subsequently connected to a second, sterile delivery device (not shown) to sterilize the system 10 for a new procedure.

In some embodiments, a plurality of disposable delivery devices similar to the delivery device 12 are provided with corresponding disposable cassettes, such as the cassette 212 for each delivery device. Individually pre-tuning the devices to an appropriate ultrasonic energy frequency, such as that previously described, before delivery to the user removes a need to test and adjust power signal parameters or delivery device configurations prior to or during each procedure. Instead, in some implementations, a single use cassette/delivery device kit is set up or configured prior to delivery to the end user, is then used in a treatment procedure, and is optionally discarded at the end of the procedure, thereby reducing operation time, a requisite skill level for "tuning" the system 10, and/or additional components or systems for tuning the delivery device 12. Moreover, the combination of the cassette 212 and delivery device 12 eliminates a need to sterilize equipment before a procedure, as all components that come into contact with bodily fluids are pre-sterilized and discarded at the end of the procedure.

According to various embodiments, the system 10 is used in any of a variety of procedures. In some embodiments, the system 10 is used to perform an ultrasound-guided percutaneous tenotomy. Some methods include the target tissue site 400 being pathologic tissues (e.g., a region of scar tissue associated with a tendon 410), where the pathologic tissue is identified using high frequency ultrasonic imaging, the tip portion 24 is percutaneously delivered, and in particular the distal section 24A, to the target tissue site 400 under ultrasonic imaging, and ultrasonic energy is delivered through the cannula 90 to debride the musculoskeletal tissue (e.g., scar tissue) forming the target tissue site 400. Some methods include identifying the target tissue site 400 entirely at the time of a procedure without cutting the skin of the patient. As previously described, in some embodiments the delivery device 12 is pre-tuned to deliver ultrasonic energy at a frequency that reduces the likelihood of trauma to healthy soft tissue while promoting debridement of the pathologic tissue. Moreover, the percutaneous, minimally invasive nature of such a procedure facilitates access and treatment of such body tissue as part of an office-based procedure under local anesthesia.

According to some methods, after the target tissue is treated and the distal section 24A of the tip portion 24 is removed from the patient, the patient is discharged to home after a short period of in-office observation due to the minimally invasive nature of the procedure (e.g., as no local anesthesia would be necessary). For example, in similarly non-invasive procedures, post-procedure pain is typically variable, but often ranges from essentially no pain to moderately severe pain lasting less than 72 hours. Thus, various embodiments of the system 10 provide for an office-based procedure under local anesthesia, thereby resulting in cost-savings to the patient by avoiding the costs of operating room time, where a patient may only need ice or cooling packs for analgesia and edema control after the treatment.

Although the present invention has been described with reference to various examples, persons skilled in the art will recognize that changes may be made in form and detail without departing from the spirit and scope of invention. For example, various modifications and additions can be made to the exemplary embodiments discussed without departing from the scope of invention. While the embodiments described above refer to particular features, the scope of invention also includes embodiments having different combinations of features and embodiments that do not include all of the above described features.

The invention claimed is:

1. A method of delivering ultrasonic energy for a debridement of musculoskeletal tissue, the method comprising:
   connecting a delivery device to a vacuum source, a fluid source, and a power signal source;
   generating ultrasonic energy by sending a power signal from a power signal source to an ultrasonic transducer that is secured coaxially about a mounting post, the transducer and mounting post being contained within a housing;
   transmitting the ultrasonic energy from the ultrasonic transducer to a cannula, at least a portion of the cannula also being contained within the housing;
   percutaneously inserting at least a portion of the cannula proximal to a musculoskeletal tissue site;
   delivering fluid from a fluid source to an exposed portion of the cannula; and
   activating a vacuum source to remove fluid delivered from the fluid source,
   wherein the vacuum source is inactivated if fluid flow to the vacuum source is undesirably reduced;
   wherein the exposed portion of the cannula is optimized to deliver ultrasonic energy at a frequency of 25 kHz to 29 kHz; and
   wherein the exposed portion of the cannula is imaged by an ultrasound imaging device during the insertion and the debridement of the musculoskeletal tissue.

2. The method of claim 1, wherein the delivery device is integrally connected to a removable cassette, wherein the removable cassette provides the connection between the delivery device and the vacuum source, the fluid source, and the power signal source.

3. The method of claim 2, wherein the delivery device and the removable cassette are disposable.

4. The method of claim 2 further comprising replacing the delivery device and removable cassette with a second delivery and a second removable cassette, wherein the second delivery device is integrally connected to the second removable cassette.

5. The method of claim 4, wherein the second delivery device and the second removable cassette are disposable.

6. The method of claim 1, wherein fluid flow to the vacuum source is undesirably reduced when there is an occlusion in the fluid flow to the vacuum source.

7. The method of claim 1, wherein fluid flow to the vacuum source is undesirably reduced when there is an interruption in the fluid flow from the fluid source.

8. The method of claim 1, further comprising percutaneously inserting the tip portion to a musculoskeletal tissue site.

9. The method of claim 8, further comprising debriding musculoskeletal tissue with the ultrasonic energy delivered from the cannula while ultrasonically imaging the tip portion of the delivery device.

10. The method of claim 1, wherein the exposed portion of the cannula comprises a tip that is cylindrical and does not have serrated edges.

11. A method of delivering ultrasonic energy for a debridement of musculoskeletal tissue, the method comprising:
   connecting a delivery device to a vacuum source, a fluid source, and a power signal source;
   generating ultrasonic energy by sending a power signal from a power signal source to an ultrasonic transducer that is secured coaxially about a mounting post, the transducer and mounting post being contained within a housing;
   transmitting the ultrasonic energy from the ultrasonic transducer to a cannula, the ultrasonic energy being delivered to the musculoskeletal tissue from an exposed portion of the cannula, at least a portion of the cannula also being contained within the housing;
   percutaneously inserting at least a portion of the cannula proximal to a musculoskeletal tissue site;
   delivering fluid from a fluid source to the exposed portion of the cannula; and
   activating a vacuum source to remove fluid delivered from the fluid source,
   wherein an interruption in the fluid flow to the vacuum source generates a signal that inactivates the power signal source;
   wherein the exposed portion of the cannula is optimized to deliver ultrasonic energy at a frequency of 25 kHz to 29 kHz; and
   wherein the exposed portion of the cannula is imaged by an ultrasound imaging device during the insertion and the debridement of the musculoskeletal tissue.

12. The method of claim 11, wherein the delivery device is integrally connected to a removable cassette, wherein the removable cassette provides the connection between the delivery device and the vacuum source, the fluid source, and the power signal source.

13. The method of claim 12, wherein the delivery device and the cassette are disposable.

14. The method of claim 12 further comprising replacing the delivery device and removable cassette with a second delivery device and a second removable cassette, wherein the second delivery device is integrally connected to the second removable cassette.

15. The method of claim 14, wherein the second delivery device and the second removable cassette are disposable.

16. The method of claim 11, wherein fluid flow to the vacuum source is undesirably reduced when there is an occlusion in the fluid flow to the vacuum source.

17. The method of claim 11, wherein fluid flow to the vacuum source is undesirably reduced when there is an interruption in the fluid flow from the fluid source.

18. The method of claim 11, further comprising percutaneously inserting the tip portion to a musculoskeletal tissue site.

19. The method of claim 18, further comprising debriding musculoskeletal tissue with the ultrasonic energy delivered from the cannula while ultrasonically imaging the tip portion of the delivery device.

20. The method of claim 11, wherein the exposed portion of the cannula comprises a tip that is cylindrical and does not have serrated edges.

* * * * *